United States Patent [19]
Subrini

[11] Patent Number: 5,088,477
[45] Date of Patent: Feb. 18, 1992

[54] PENILE FILLING IMPLANT

[76] Inventor: Louis Subrini, 27 Boulevard Suchet, 75016 Paris, France

[21] Appl. No.: 618,283

[22] Filed: Nov. 28, 1990

[30] Foreign Application Priority Data

Nov. 28, 1989 [FR] France ............... 89 15620

[51] Int. Cl.$^5$ .............................................. A61F 2/26
[52] U.S. Cl. .............................................. 600/40
[58] Field of Search ................................. 128/79

[56] References Cited

U.S. PATENT DOCUMENTS

| | | | |
|---|---|---|---|
| 3,832,996 | 9/1974 | Kalnberz | 128/79 |
| 4,066,073 | 1/1978 | Finney et al. | 128/79 |
| 4,267,829 | 5/1981 | Burton et al. | 128/79 |
| 4,335,714 | 6/1982 | Edgarton et al. | 128/79 |
| 4,628,912 | 12/1986 | Fischell | 128/79 |
| 4,881,531 | 11/1989 | Timm et al. | 128/79 |

*Primary Examiner*—Cary E. O'Connor
*Attorney, Agent, or Firm*—Larson and Taylor

[57] ABSTRACT

A penile filling implant is disclosed in the form of an elongate synthetic material body (1) of a thickness generally greater than about 10 mm, characterized in that it is substantially more flexible and softer, permanently and at all points of its mass, than known prostheses, so as to avoid conferring permanent rigidity on the penis while being adapted to form a total or sub-total filling element of the cavity, as a function of the length proper to each individual.

12 Claims, 1 Drawing Sheet

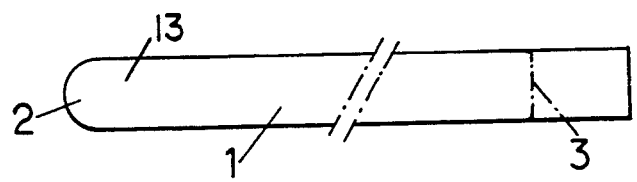
FIG.1.
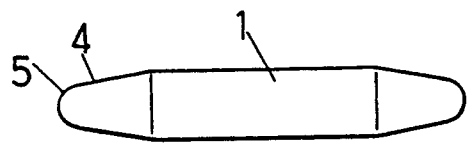
FIG.2.
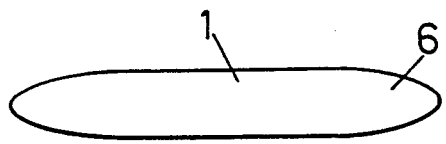
FIG.3.
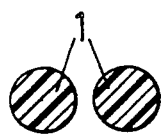  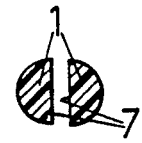
FIG.4.   FIG.5.   FIG.6.
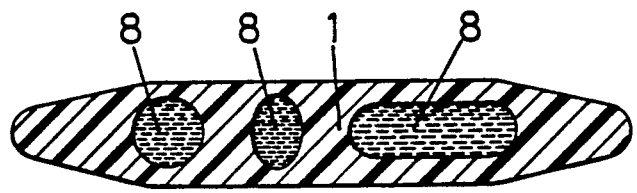
FIG.7.
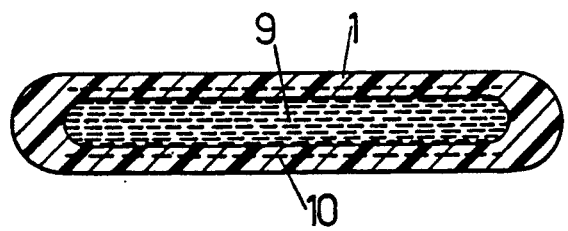
FIG.8.
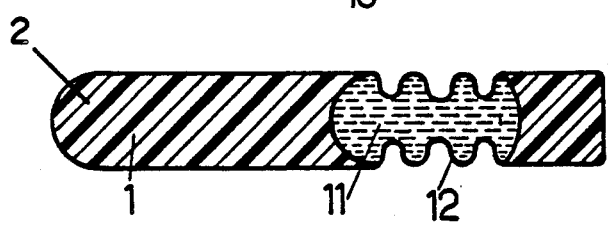
FIG.9.

PENILE FILLING IMPLANT

BACKGROUND OF THE INVENTION

Up to now attempts have been made to overcome certain cases of impotence (those which had especially organic causes) by "mechanical means" such as prostheses introduced by a surgical operation into the corpus cavernosum of the penis. Several types of prostheses have been developed, which all have the essential purpose of permanently or temporarily conferring an artificial rigidity on the penis.

Certain prostheses with permanent rigidity are made from a relatively rigid synthetic material and extend through all or part of the corpus cavernosum. Some have over practically half their length a relatively slightly rigid proximal part intended to occupy the perineal zone of the corpus cavernosum and a more rigid end or distal part following the first and occupying the whole penile part of the corpus cavernosum.

Other prostheses made from a synthetic material are pliable, having for this on the inside a braid of silver threads. The drawback of these prostheses resides in the stiffness which they confer on the penis, and in a relatively rapid breakage of the braid, following successive folding to which it is subjected, which then requires replacement.

The permanent rigidity conferred on the penis and in particular on his distal part by all these systems is an obvious drawback. There also exists a large variety of prostheses with temporary rigidity. They generally comprise an internal cavity inflatable by a pressurized fluid, whose reservoir is either contained also in the prosthesis and may be brought into service by a pressure exerted thereon from the outside, or is disposed on the outside, being then implanted in the vicinity in the body of the subject and connected to the cavities in question by fluid ducts.

These prostheses are composite, comprise mechanisms which may in the long run deteriorate, even if they are simple, and are obviously unpleasant to use.

SUMMARY OF THE INVENTION

The aim of the present invention is to overcome all these drawbacks of the prior art.

The invention is based on the surprising discovery that the presence alone of a filling body, even if it is not rigid, of sufficient volume - in the cavernous bodies is sufficient, at least in the cases where the impotence is not absolute, to permit a practically natural erection.

As is known, the erection begins by a surge of blood through the cavernous artery, which inflates the cavernous sinuses; when they are sufficiently inflated, the sub-albuginean venous network is thus compressed enough to prevent the blood from being discharged, which maintains the rigidity of the corpus cavernosum.

The explanation of the phenomenon observed when an implant of a certain volume is introduced into the corpus cavernosum then that, since this implant occupies a relatively large part of the normal volume of the cavernous sinuses, a much smaller part of this volume is able to be fed by the blood from the cavernous artery; thus, the remaining sinuses, situated about the implant, may be much more rapidly filled with blood and may again compress the sub-albuginean venous network, which will produce and maintain a practically natural erection.

These discoveries show that it was in actual fact quite useless to employ rigid prostheses in all cases, since a relatively soft implant makes it possible to obtain just as well the result which has just been mentioned, without the disadvantage inherent in prostheses with permanent rigidity.

A penile implant according to the invention which, like known prostheses, will generally be in the form of an elongate body made from synthetic material, of a thickness generally equal to or greater than 10 or 13 mm, will then be essentially characterized in that it is substantially permanently more flexible and softer at least in the penile or distal segment of the implant, than known prostheses, so as to avoid conferring obligatorily on the penis a permanent rigidity, while being adapted to form a total or sub-total filling element of the cavernous body, as a function of the length proper to each individual.

As synthetic material, any appropriate material tolerated by the tissues may be used, and in particular silicone.

Considering the desired aim, such as discussed above, this material may have advantageously, permanently and at every point of its mass at least in the penile or distal segment of the implant, a modulus of elasticity less than about 50 kg/cm$^2$ for a relative extension of 100%, this modulus being preferably less than 35 kg/cm$^2$, and dropping even in some cases to 5 kg/cm$^2$, still for 100% relative extension, this modulus of elasticity being, for the plastic materials concerned, fairly well representative of the flexibility of the material.

By way of comparison, the prostheses with differentiated rigidity discussed above may have a modulus of elasticity (still for 100% relative extension) of about 50 to 53 kg/cm$^2$ for the most rigid distal part, and dropping to 6 kg/cm$^2$ for the most flexible part of the prosthesis.

Another parameter for distinguishing an implant according to the invention from the prostheses of the prior art is the hardness of the material which forms it.

The synthetic material used may advantageously have, at least in the penile or distal segment of the implant, a hardness less than about 70 Shore A, while remaining greater than about 5 Shore A. Preferably this hardness will be of the order of about 35 Shore A.

By way of comparison, the prostheses with differentiated rigidity discussed above may have a hardness of about 65 to 75 Shore A for the most rigid distal part and from 30 to 40 Shore A for the most flexible part.

None of the prostheses of the prior art of course has, at every point of its mass and in particular at the penile segment, a modulus of elasticity or a permanent hardness as low as those which have been mentioned above for an implant according to the invention.

BRIEF DESCRIPTION OF THE DRAWINGS

Other characterstics of implants according to the invention, particularly as to their form and structure, will now be described below with reference to the figures of the accompanying drawing in which:

FIG. 1 represents an implant according to the invention adapted to be cut to the desired length.

FIG. 2 shows another implant of the invention.

FIG. 3 shows another implant of the invention.

FIGS. 4 to 6 shows different forms of cross sections.

FIGS. 7 and 8 show implants according to the invention with internal cavities, and FIG. 9 shows an implant of the invention having an internal cavity.

DETAILED DESCRIPTION OF THE INVENTION

In FIG. 1, a length of a cylindrical and rectilinear elongate body 1 made from silicone has been shown, with constant cross section and from 10 to 13 and even 14 or 15 mm in diameter. A penile segment 13 has a distal end 2 which is rounded in a sphere portion. By cutting elongate body 1 as indicated at 3, an implant may then be obtained of the desired length. End 3 may be slightly rounded with a cutting instrument to avoid any sharp angle.

In FIGS. 2 and 3 on the contrary, each of the implants shown is of a predetermined length and has a cylindrical elongate body 1 which ends in a truncated cone 4 and a spherical part 5 (FIG. 2) or ends in an ogive 6 with slightly rounded tip (FIG. 3). The implants of FIGS. 2 and 3 have their two ends symmetrical with each other with respect to the transverse median plane of body 1.

In FIGS. 4, 5 and 6 two implants have been shown in cross section assumed to be disposed one at the side of the other in the corpus cavernosum of the penis. The cross section may be circular (FIG. 4) or oval (or elliptic) as can be seen in FIG. 5.

Bodies 1 may also comprise lateral flattened portions 7, the flattened portions of the bodies implanted in the corpus cavernosum of the penis being thus able to face each other (FIG. 6).

It should be noted that in the case of a sub-total filling implant, it may be allowed to move in each of the cavernous bodies, assuming that an axial passage is formed therein, or on the contrary it may be fixed in a given position, advantageously the perineal zone, by a suture or any other means.

In all cases, the rounded shapes of the ends which have been described above are very appropriate since they correspond substantially to the form of the ends of the cavernous bodies.

In FIGS. 7 and 8 the possibility has been shown of not using solid and homogenous bodies 1 as in the case of FIGS. 1 to 6, but bodies 1 with internal cavities 8 of varied shapes (FIG. 7) or with a single internal cavity 9 (FIG. 8).

Cavities 8 of FIG. 7 have different forms which may be met with separately on different implants but it will be understood that on one and the same implant they will all generally have the same shape; it is only so as not to increase the number of figures that different shapes have been shown in FIG. 7; in any case, the cavities may communicate with each other and be filled, either during implantation or subsequently, with any pressurized fluid, such as silicone gel, which allows the dimensions of the implant or its characteristics of flexibility or hardness to be adjusted.

The form of the cavity or cavities and the direction of their extension may be further chosen as a function of the dimension it is desired to increase (cross section or length of the implant).

With such implants, as with that of FIG. 8, a progressive extension of a penis of insufficient dimensions may be obtained by progressively increasing the dimensions of the implants, without the need of operating for removing them and replacing them. In fact, the pressurized fluid may be conveniently injected into the internal cavities of the implant by means of a needle, a very simple self closing device then preventing this fluid from escaping, unless it is tapped for any reason, for example for reducing the dimensions of the implant.

It should also be noted that the presence of cavities filled or not with a fluid, inside the implant, makes it possible to give it a hardness less than that which it would have if it were formed of a solid and homogeneous body; its hardness may thus be reduced below the minimum values which it is possible to obtain at the present time with a normal medical silicone, whose minimum hardness is 20 Shore A.

In another variant according to the invention, an inextensible reinforcement 10 such as a latticework, a fabric or similar may be embedded in the synthetic material forming the body, about the cavity, to form a sheath or spiral about the cavity in order to prevent expansion of the cavity even when pressurized fluid is injected therein. This provides an additional possibility, which is to increase the hardness of the implant without increasing its dimensions. The implant may then be adapted to all cases.

It may further be mentioned that the implant according to the invention may be further distinguished from all known prostheses, whose diameter never exceeds 13 mm. An implant according to the invention, if it is not rigid, may in fact have a substantially greater diameter or thickness, namely of the order of 14 and even 15 mm.

In the embodiment of FIG. 9, implant 1 comprises a cavity 11 whose wall comprises a bellows portion 12 a substantial distance away from the distal end 2. The injection of the pressurized fluid into the cavity will cause progressive extension of the penis. By increasing this pressure in several steps, it is possible to obtain considerable total tissue extension or expansion, the implant being able to extend itself in appreciable proportions and cause the extension of the penis by the internal pressure which it exerts on the gland.

If it is desired to remedy both impotence and a penis length which is too small, this implant may be left permanently in position. If there is no impotence, this implant may be withdrawn as soon as the penis has acquired the desired length.

It should finally be noted that an implant according to the invention, in all its variants, may be much shorter than the penis and so be implanted only, either in the proximal part or in the distal part thereof, depending on the needs.

I claim:

1. A penile filling implant comprising:
   an elongate body of synthetic material having a thickness of at least about 10 mm, said elongated body including a penile segment for filling a portion of the corpus cavernosum of the penis, at least said penile segment having a modular of elasticity less than about 50 kg/cm$^2$ for a relative extension of 100% and a hardness between about 5 and 70 Shore A.

2. The implant according to claim 1, wherein said penile segment has a modulus of elasticity between about 5 and 35 kg/cm$^2$ for a relative extension of 100% and a hardness of about 35 Shore A.

3. The implant according to claim 1, wherein said synthetic material comprises silicone.

4. The implant according to claim 1, wherein said elongate body has a constant cross section with the exception of at least one end of said elongate body.

5. The implant according to claim 4, wherein said elongate body includes a flattened portion for facing a flattened portion on a second elongated body filling a portion of the corpus cavernosum of the penis.

6. The implant according to claim 1, wherein said elongate body includes ends in the shape of truncated cones, said ends ending in a spherical portion.

7. The implant according to claim 1, wherein said elongate body includes ends that are in the shape of an ogive.

8. The implant according to claim 1, wherein said elongate body includes ends that are symmetrical with each other with respect to a median transverse plane of the body.

9. The implant according to claim 1, wherein said elongate body includes at least one cavity.

10. The implant according to claim 9, wherein said at least one cavity is filled with a pressurized fluid.

11. The implant according to claim 9, wherein an inextensible reinforcement is embedded in synthetic material surrounding said cavity to allow fluid injected into said cavity to increase the hardness of said implant without increasing the size of said implant.

12. The implant according to claim 9, wherein said at least one cavity includes a lateral wall comprising a bellows for extending the penis when said bellows is filled, said bellows being located a substantial distance away from a distal end of said penile segment.

* * * * *